United States Patent [19]

Tahara et al.

[11] Patent Number: 4,782,057
[45] Date of Patent: Nov. 1, 1988

[54] BENZO[H]CINNOLINE COMPOUND, A METHOD OF PREPARING SAID COMPOUND AND A PHARMACEUTICAL COMPOSITION

[75] Inventors: Tetsuya Tahara, Nakatsu; Minoru Kawakami, Chikujo; Shuzo Takehara, Nakatsu; Masamitsu Sakamori, Chikujo, all of Japan

[73] Assignee: Yoshitomi Pharmaceutical Industries, Ltd., Osaka, Japan

[21] Appl. No.: 848,371

[22] PCT Filed: Aug. 26, 1985

[86] PCT No.: PCT/JP85/00471
 § 371 Date: Mar. 25, 1986
 § 102(e) Date: Mar. 25, 1986

[87] PCT Pub. No.: WO86/01506
 PCT Pub. Date: Mar. 13, 1986

[30] Foreign Application Priority Data

Aug. 28, 1984 [JP] Japan ................... 59-178789

[51] Int. Cl.⁴ .................. C07D 237/36; A61K 31/50
[52] U.S. Cl. .................. 514/248; 544/234; 562/462; 562/490; 568/328
[58] Field of Search .................. 514/248; 544/234

[56] References Cited

U.S. PATENT DOCUMENTS 3,464,988 9/1969 Holava et al. .................. 544/234
4,602,019 7/1986 Sircar et al. .................. 544/234

FOREIGN PATENT DOCUMENTS 124314 11/1984 European Pat. Off. .................. 544/234
169443 1/1986 European Pat. Off. .

OTHER PUBLICATIONS

Curran, Ross; J. Med. Chem., 17, p. 273 (1974).

Cignarella et al. I, Il Farmaco, Ed. Sci., 37(2), p. 133 (1981).
Yamada et al., J. Med. Chem., 25, p. 975 (1982).
Tebib et al., Chemical Abstracts, vol. 108, No. 31317m (1988).

Primary Examiner—Donald G. Daus
Assistant Examiner—E. Bernhardt
Attorney, Agent, or Firm—Wenderoth, Lind & Ponack

[57] ABSTRACT

A benzo[h]cinnoline compound of the formula:

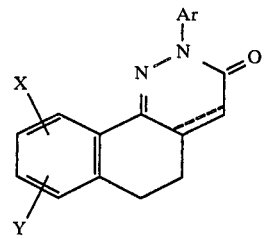

wherein each of X and Y is hydrogen, halogen, trifluoromethyl, hydroxy, alkyl having 1 to 4 carbon atoms, alkoxy having 1 to 4 carbon atoms, amino, alkanoylamido having 2 to 4 carbon atoms, nitro, cyano, alkanoyl having 2 to 4 carbon atoms; Ar is phenyl or pyridyl which may be optionally substituted by at least one substituent selected from the group consisting of halogen, trifluoromethyl, hydroxy, alkyl having 1 to 4 carbon atoms, alkoxy having 1 to 4 carbon atoms, amino, alkanoylamido having 2 to 4 carbon atoms, nitro and cyano; and the bond position indicated by dotted line is single bond or double bond, a method of preparing said compound and a pharmaceutical composition containing said compound.

Since these compounds possess high affinity for benzodiazepine receptor and antianxiety activity, they are useful as neutralizers to an excess dose of antianxiety agents or as antianxiety agents.

9 Claims, No Drawings

BENZO[H]CINNOLINE COMPOUND, A METHOD OF PREPARING SAID COMPOUND AND A PHARMACEUTICAL COMPOSITION

FIELD OF THE ART

The present invention relates to novel and pharmaceutically useful benzo[h]cinnoline compounds, methods of preparing said compounds and pharmaceutical compositions containing said compounds.

PRIOR ART

Journal of Medicinal Chemistry (J. Med. Chem.), Vol. 14, p. 262 (1971) discloses 2-substituted-benzo[h]cinnolin-3(2H)-ones. This literature reports that all the compounds were found to be devoid of significant biological activity, although all the compounds were evaluated for analgesic, hypotensive, antiinflammatory, and CNS activities.

European Patent Application No. 124314 discloses 3H-indeno-pyridazin-3-one derivatives with cardiotonic and antihypertensive activities.

DISCLOSURE OF THE INVENTION

The present inventors have made intensive studies in order to develop useful drugs. As a result of such investigations, the present inventors have found that novel benzo[h]cinnoline compounds have potent affinity for benzodiazepine receptor and antianxiety activity. The present invention, relates to benzo[h]cinnoline compounds represented by the formula:

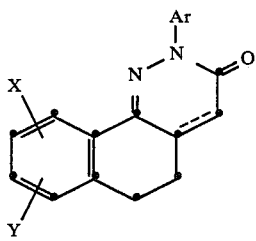

In the formula, each of X and Y is hydrogen, halogen (e.g. fluorine, chlorine or bromine), trifluoromethyl, hydroxy, alkyl having 1 to 4 carbon atoms (e.g. methyl, ethyl, propyl, isopropyl, butyl or isobutyl), alkoxy having 1 to 4 carbon atoms (e.g. methoxy, ethoxy, propoxy or butoxy), amino, alkanoylamido having 2 to 4 carbon atoms (e.g. acetamido, propionamido or butyrylamido), nitro, cyano, alkanoyl having 2 to 4 carbon atoms (e.g. acetyl, propionyl or butyryl); Ar is phenyl or pyridyl which may be optionally substituted by at least one substituent selected from the group consisting of halogen (e.g. fluorine, chlorine or bromine), trifluoromethyl, hydroxy, alkyl having 1 to 4 carbon atoms (e.g. methyl, ethyl, propyl, isopropyl, butyl or isobutyl), alkoxy having 1 to 4 carbon atoms (e.g. methoxy, ethoxy, propoxy or butoxy), amino, alkanoylamido having 2 to 4 carbon atoms (e.g. acetamido, propionamido or butyrylamido), nitro and cyano; and the bond position indicated by dotted line is single bond or double bond.

The compounds of formula (I) of the present invention can be, for example, prepared by the following Methods 1, 2 and 3.

(1) Method 1

The compound of the formula (I) can be prepared by reacting a compound of the formula:

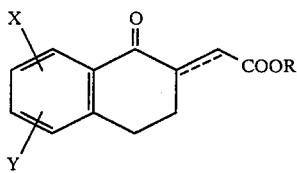

wherein R is hydrogen or alkyl having 1 to 4 carbon atoms (e.g. methyl, ethyl, propyl, isopropyl, butyl or isobutyl) and other symbols are as defined above, with a hydrazine compound of the formula:

 ArNHNH$_2$ (III)

wherein Ar is as defined above, or acid addition salt thereof (e.g. hydrochloric acid salt), and then subjecting the thus obtained compound of the formula:

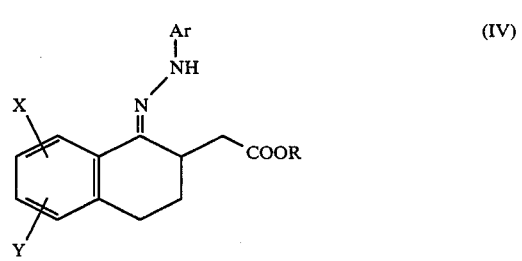

wherein each symbol is as defined above, to a ring closure reaction.

The reaction of the compound of the formula (II) with the compound of formula (III) is carried out by refluxing under heating for 5 to 20 hours in a suitable solvent, for example, in an alcoholic solvent such as methanol, ethanol or propanol. In case the hydrazine compound of formula (III) is used as an acid addition salt, the above reaction is carried out in the presence of an acid scavenger (e.g. sodium acetate, potassium acetate, sodium hydrogencarbonate, sodium carbonate or potassium carbonate).

The ring closure reaction of the obtained compound of formula (IV) is carried out by refluxing under heating for 5 to 10 hours in acetic acid.

(2) Method 2

The compound of the formula (I), wherein the bond position indicated by dotted line is double bond, can be synthesized by adding bromine in acetic acid dropwise to the compound wherein the bond position indicated by dotted line is single bond [Journal of Medicinal Chemistry (J. Med. Chem.), Vol. 14, p. 262 (1971)], and preferably by adding 1 to 1.5 times moles of bromine dropwise to the compound of the formula:

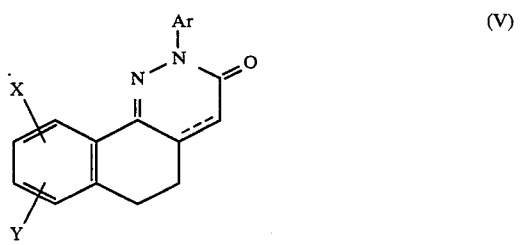

wherein each symbol is as defined above, at 20°–60° C. in acetic acid.

The compound of the formula (I) wherein the bond position indicated by the dotted line is a double bond can also be prepared by reacting the compound wherein the bond position indicated by a dotted line is a single bond with sodium m-nitrobenzenesulfonate (Backmann Method, British Pat. No. 1,168,291.

(3) Method 3

The substituent X, Y or Ar of the compound obtained by the foregoing Method 1 or 2 is converted into other substituent(s) according to conventional manners of organic chemical synthesis.

Such methods include, for example, reduction of a nitro group to an amino group; acylation of an amino group with a lower alkanoic acid; and conversion of an amino group into a cyano group (e.g. Sandmeyer reaction or Gattermann reaction).

When binding affinity for benzodiazepine receptor of the compounds of formula (I) thus obtained was measured by using a labeled-diazepam with tritium as a ligand, it has been found that said compounds possess high affinities for benzodiazepine receptor of from $10^{-7}$ to $10^{-9}$ M, and so they are useful as neutralizers to an excess dose of antianxiety agents. Furthermore, since some compounds exhibit an anti-pentylenetetrazole activity, they are also useful as antianxiety agents. The compounds of the present invention, when used as drugs, are advantageous because they do not show sedative activity.

A displacement ability for benzodiazepine receptor is shown as follows:

Experimental method:

A specific binding for benzodiazepine receptor was determined according to the methods described in European Journal of Pharmacology, vol. 51, p. 129 (1978) and Life Science, vol. 20, p. 1201 (1977).

In brief, the crude synaptosomal membranes were prepared from the cerebral cortex of 9 to 10 week-old male Wistar rats and were suspended in Tris-HCl buffer (pH 7.4). Various concentrations of test compounds and tritiated diazepam (final concentration: 2 nM) were incubated at 4° C. for 20 minutes. Then the suspension was filtered through Whatman GF/B glass fiber filters. Radioactivity of tritiated diazepam on the filters was measured by liquid scintillation spectrometry. Specific binding was defined as the difference in the amount of radioactivity bound in the absence and presence of $1.0 \times 10^{-6}$ M unlabeled diazepam.

According to the above experimental method, the affinity of the compounds of the present invention is evaluated as an ability to displace tritiated diazepam from the binding site, and is represented as Ki value. The results are summarized in the Table 1.

TABLE 1

| Test Compound (Example No.) | K i (M) | Test Compound (Example No.) | K i (M) |
| --- | --- | --- | --- |
| 1 | $1.2 \times 10^{-7}$ | 15 | $2.8 \times 10^{-8}$ |
| 2 | $1.9 \times 10^{-7}$ | 16 | $1.4 \times 10^{-8}$ |
| 3 | $1.3 \times 10^{-7}$ | 17 | $4.7 \times 10^{-8}$ |
| 11 | $1.6 \times 10^{-8}$ | 18 | $9.0 \times 10^{-8}$ |
| 12 | $2.6 \times 10^{-8}$ | 19 | $4.5 \times 10^{-8}$ |
| 13 | $6.6 \times 10^{-9}$ | 20 | $3.4 \times 10^{-8}$ |
| 14 | $8.2 \times 10^{-9}$ | 30 | $2.2 \times 10^{-7}$ |

Acute toxicity

The compound of Example 13 was orally or intraperitoneally administered to mice. All mice survived at the oral dose of 1000 mg/kg and at the intraperitoneal dose of 250 mg/kg.

The compounds of the present invention, when used as drugs, can be administered in the form of pharmaceutical composition such as tablets, capsules, granules, powder, syrup, injectable solutions, suppositories or the like by mixing a therapeutically effective amount of the compound of the present invention with pharmaceutically acceptable additives (excipient, carrier, diluent and so on). The daily dose, for example, in an oral administration for human adults usually ranges from 5 mg to 500 mg in a single or multiple doses.

Formulation Example

The tablets containing 20 mg of the compound (I) of the present invention can be prepared by the following composition.

| | |
| --- | --- |
| Compound (I) | 20.0 mg |
| Lactose | 68.5 mg |
| Corn starch | 30.0 mg |
| Crystalline cellulose | 20.0 mg |
| polyvinyl pyrrolidone K-30 | 2.0 mg |
| Talc | 4.0 mg |
| Magnesium stearate | 0.5 mg |
| | 145.0 mg |

Compound (I) is crushed with an atomizer to make a fine powder having an average particle size below 10 μ. The fine powder of Compound (I), lactose, corn starch and crystalline cellulose are mixed well in a kneader and then kneaded with a binder prepared by polyvinyl pyrrolidone. The wet mass is passed through a 200 mesh sieve and then dried in an oven at 50° C. The dry granule containing 3–4% of water content is forced through a 24 mesh sieve. Talc and magnesium stearate are mixed and compressed into tablets by using a rotatory tableting machine with a flat punch of 8 mm diameter.

The present invention will be explained by the following examples in more detail, but these examples are not to be construed as limiting the present invention:

EXAMPLE 1

A mixture of 12 g of 7-chloro-1,2,3,4-tetrahydro-1-oxo-2-naphthaleneacetic acid and 8.1 g of phenylhydrazine in 150 ml of ethanol is refluxed under heating for 14 hours. Then the ethanol is distilled off under reduced pressure, 100 ml of acetic acid is added to the residue and the mixture is refluxed under heating for 7 hours. After the acetic acid is distilled off, the residue is extracted with chloroform. The extract is washed with water, dried over magnesium sulfate anhydride and then the chloroform is distilled off to give crystals. The precipitated crystals are collected by filtration and recrystallized from alcohol to give 11.1 g of 9-chloro-2-phenyl-4,4a,5,6-tetrahydrobenzo[h]cinnolin-3(2H)-one as colorless prisms, melting at 120°–122° C.

EXAMPLE 2

About half volume of 10 ml of solution of 3.9 g of bromine in acetic acid is added dropwise to a solution of 5 g of 9-chloro-2-phenyl-4,4a,5,6-tetrahydrobenzo[h]cinnolin-3(2H)-one in 150 ml of acetic acid with stirring at room temperature. After the mixture is heated up to 50° C. on a water bath, the remaining solution is added dropwise. After stirring under heating at 50° C. for 2 hours, the precipitated crystals are collected by filtration, washed with water and recrystallized from ethanol to give 2.7 g of 9-chloro-2-phenyl-5,6-dihydrobenzo[h]cinnolin-3(2H)-one as yellow leaflets, melting at 184°–186° C.

EXAMPLE 3

A mixture of 5 g of 1,2,3,4-tetrahydro-1-oxo-2-naphthylideneacetic acid and 3 g of phenylhydrazine in 100 ml of ethanol is refluxed for 10 hours. The precipitated crystals are collected by filtration, washed with ethanol and dissolved in 50 ml of acetic acid. The solution is refluxed under heating for 8 hours and the acetic acid is distilled off. The residue is extracted with ethyl acetate and the extract is washed with an aqueous sodium hydrogencarbonate solution. After drying over magnesium sulfate anhydride, the solvent is distilled off and to the residue is added ethanol. The precipitated crystals are collected by filtration and recrystallized from ethanol to give 1.4 g of 2-phenyl-5,6-dihydrobenzo[h]cinnolin-3(2H)-one as pale yellow needles, melting at 155°–157° C.

EXAMPLE 4

After a mixture of 7-trifluoromethyl-1,2,3,4-tetrahydro-1-oxo-2-naphthaleneacetic acid and phenylhydrazine in ethanol is refluxed under heating for 10 hours, the ethanol is distilled off. To the residue is added acetic acid and the mixture is refluxed under heating for 7 hours. After the acetic acid is distilled off, the residue is extracted with chloroform and the extract is washed with water and dried over magnesium sulfate anhydride. The chloroform is distilled off to give 2-phenyl-9-trifluoromethyl-4,4a,5,6-tetrahydrobenzo[h]cinnolin-3(2H)-one.

7-Trifluoromethyl-1,2,3,4-tetrahydro-1-oxo-2-naphthaleneacetic acid as a starting substance can be obtained as follows:

To an aqueous solution of sodium metaperiodate (NaIO$_4$) is added a small amount of concentrated sulfuric acid with stirring. A solution of tartaric acid dissolved in water at 12°–24° C. is added dropwise to the mixture with cooling at 12°–30° C. After the mixture is stirred at room temperature for 30 minutes, 7-trifluoromethyl-α-tetralone is added. An aqueous solution of sodium hydroxide is added dropwise below 30° C., and then ethanol is added. The reaction mixture is stirred at room temperature for 15 hours and further heated at 50°–60° C. for 4 hours. The resulting mixture is filtered and the filtrate is concentrated to about half of volume. The concentrated filtrate is acidified with concentrated hydrochloric acid on cooling to give 7-trifluoromethyl-1,2,3,4-tetrahydro-1-oxo-2-naphthylideneacetic acid.

Furthermore, to a solution of the obtained 7-trifluoromethyl-1,2,3,4-tetrahydro-1-oxo-2-naphthylideneacetic acid in acetic acid are added water and zinc powder. The mixture is stirred under heating at 60° C. for 1 hour on a water bath and resultant mixture is filtered. The filtrate is concentrated and the residue is acidified with diluted hydrochloric acid to give 7-trifluoro-methyl-1,2,3,4-tetrahydro-1-oxo-2-naphthaleneacetic acid.

EXAMPLE 5

To a mixture of 9-chloro-2-(4-nitrophenyl)-4,4a,5,6-tetrahydrobenzo[h]cinnolin-3(2H)-one in ethanol and water is added iron powder with stirring at room temperature. To the mixture is added dropwise concentrated hydrochloric acid with stirring and heating up to 60° C. on a water bath. The resulting mixture is further stirred under heating at the same temperature and filtered, then the filtrate is concentrated. After the residue is made alkaline by adding an aqueous solution of sodium hydroxide, the mixture is extracted with chloroform. The extract is washed with water and dried over magnesium sulfate anhydride. The chloroform is distilled off to give 2-(4-aminophenyl)-9-chloro-4,4a,5,6-tetrahydrobenzo[h]cinnolin-3(2H)-one.

EXAMPLE 6

A mixture of 2-(4-aminophenyl)-9-chloro-4,4a,5,6-tetrahydrobenzo[h]cinnolin-3(2H)-one in acetic anhydride is refluxed under heating for 8 hours. After the acetic anhydride is distilled off, the residue is extracted with chloroform. The extract is washed with water and dried over magnesium sulfate anhydride. The chloroform is distilled off to give 2-(4-acetamidophenyl)-9-chloro-4,4a,5,6-tetrahydrobenzo[h]cinnolin-3(2H)-one.

EXAMPLE 7

2-(4-Aminophenyl)-9-chloro-4,4a,5,6-tetrahydrobenzo[h]cinnolin-3(2H)-one is added to the mixture of water and concentrated hydrochloric acid which is cooled on an ice bath and then an aqueous solution of sodium nitrite is added dropwise. The mixture is stirred under ice-cooling for 30 minutes and then neutralized with sodium carbonate. The solution is added dropwise with stirring to a solution of cuprous cyanide and potassium cyanide which is previously prepared. The mixture is stirred under ice-cooling for 30 minutes and allowed to stand overnight at room temperature. The precipitated crystals are collected by filtration to give 9-chloro-2-(4-cyanophenyl)-4,4a,5,6-tetrahydrobenzo[h]cinnolin-3(2H)-one.

EXAMPLE 8

A solution of 7-nitro-1,2,3,4-tetrahydro-1-oxo-2-naphthaleneacetic acid and phenylhydrazine in ethanol is refluxed under heating for 10 hours. The ethanol is distilled off and to the residue is added acetic acid and then the resulting mixture is refluxed under heating for 8 hours. After the acetic acid is distilled off, the mixture is extracted with chloroform and the extract is washed with water. After drying over magnesium sulfate anhydride, the chloroform is distilled off to give 9-nitro-2-phenyl-4,4a,5,6-tetrahydrobenzo[h]cinnolin-3(2H)-one.

7-Nitro-1,2,3,4-tetrahydro-1-oxo-2-naphthaleneacetic acid as a starting substance can be prepared as follows:

To nitric acid (density=1.50) cooled with dry ice and methanol is added 1,2,3,4-tetrahydro-1-oxo-2-naphthaleneacetic acid at −10 to −15° C. The resulting mixture is stirred below 0° C. for 40 minutes and poured into ice. The precipitated crystals are collected by filtration to give 7-nitro-1,2,3,4-tetrahydro-1-oxo-2-naphthaleneacetic acid.

EXAMPLE 9

To a mixture of 9-nitro-2-phenyl-4,4a,5,6-tetrahydrobenzo[h]cinnolin-3(2H)-one in ethanol and water is added iron powder with stirring at room temperature. The mixture is heated up to 50° C. on a water bath with stirring and concentrated hydrochloric acid is added dropwise carefully. The resulting mixture is further stirred with heating at 80° C. and the filtrate is concentrated. To the residue is added an aqueous sodium hydroxide solution, and the alkaline solution is extracted with chloroform. The extract is washed with water, dried over magnesium sulfate anhydride and the chloroform is distilled off to give 9-amino-2-phenyl-4,4a,5,6-tetrahydrobenzo[h]cinnolin-3(2H)-one.

EXAMPLE 10

9-Amino-2-phenyl-4,4a,5,6-tetrahydrobenzo[h]cinnolin-3(2H)-one obtained by Example 9 is subjected to a similar reaction as Example 7 to give 9-cyano-2-phenyl-4,4a,5,6-tetrahydrobenzo[h]cinnolin-3(2H)-one, and the former 9-amino compound is subjected to a similar reaction as Example 6 to give 9-acetamido-2-phenyl-4,4a,5,6-tetrahydrobenzo([h]cinnolin-3(2H)-one.

The following compounds can be prepared in a similar manner as the above examples.

EXAMPLE 11

9-Methyl-2-(4-methylphenyl)-4,4a,5,6-tetrahydrobenzo[h]cinnolin-3(2H)-one, melting at 177°–178° C.

EXAMPLE 12

2-(4-Chlorophenyl)-9-methyl-4,4a,5,6-tetrahydrobenzo[h]cinnolin-3(2H)-one, melting at 143°–145° C.

EXAMPLE 13

2-(4-Methoxyphenyl)-9-methyl-4,4a,5,6-tetrahydrobenzo[h]cinnolin-3(2H)-one, melting at 146°–149° C.

EXAMPLE 14

9-Methoxy-2-(4-methylphenyl)-4,4a,5,6-tetrahydrobenzo[h]cinnolin-3(2H)-one, melting at 137°–139° C.

EXAMPLE 15

9-Chloro-2-(4-methylphenyl)-5,6-dihydrobenzo[h]cinnolin-3(2H)-one, melting at 184°–186° C.

EXAMPLE 16

9-Chloro-2-(4-methylphenyl)-4,4a,5,6-tetrahydrobenzo[h]cinnolin-3(2H)-one, melting at 135°–138° C.

EXAMPLE 17

9-Chloro-2-(4-chlorophenyl)-5,6-dihydrobenzo[h]cinnolin-3(2H)-one, melting at 205°–207° C.

EXAMPLE 18

9-Chloro-2-(4-nitrophenyl)-5,6-dihydrobenzo[h]cinnolin-3(2H)-one, melting at 258°–259° C.

EXAMPLE 19

2-(4-Chlorophenyl)-9-fluoro-5,6-dihydrobenzo[h]cinnolin-3(2H)-one, melting at 176°–179° C.

EXAMPLE 20

2-(4-Chlorophenyl)-9-fluoro-4,4a,5,6-tetrahydrobenzo[h]cinnolin-3(2H)-one, melting at 158°–160° C.

EXAMPLE 21

2-(3-Trifluoromethylphenyl)-5,6-dihydrobenzo[h]cinnolin-3(2H)-one, melting at 120°–123° C.

EXAMPLE 22

2-(4-Chlorophenyl)-5,6-dihydrobenzo[h]cinnolin-3(2H)-one, melting at 156°–159° C.

EXAMPLE 23

8-Chloro-2-(4-chlorophenyl)-5,6-dihydrobenzo[h]cinnolin-3(2H)-one, melting at 201°–203° C.

EXAMPLE 24

8-Chloro-2-(4-chlorophenyl)-4,4a,5,6-tetrahydrobenzo[h]cinnolin-3(2H)-one, melting at 175°–177° C.

EXAMPLE 25

8-Chloro-2-phenyl-5,6-dihydrobenzo[h]cinnolin-3(2H)-one, melting at 122°–124° C.

EXAMPLE 26

8-Chloro-2-phenyl-4,4a,5,6-tetrahydrobenzo[h]cinnolin-3(2H)-one, melting at 125°–127° C.

EXAMPLE 27

9-Chloro-2-(4-nitrophenyl)-4,4a,5,6-tetrahydrobenzo[h]cinnolin-3(2H)-one, melting at 177°–179° C.

EXAMPLE 28

9-Chloro-2-(4-fluorophenyl)-5,6-dihydrobenzo[h]cinnolin-3(2H)-one, melting at 174°–177° C.

EXAMPLE 29

9-Chloro-2-(4-fluorophenyl)-4,4a,5,6-tetrahydrobenzo[h]cinnolin-3(2H)-one, melting at 152°–153° C.

EXAMPLE 30

9-Fluoro-2-phenyl-5,6-dihydrobenzo[h]cinnolin-3(2H)-one, melting at 180°–181° C.

EXAMPLE 31

9-Fluoro-2-phenyl-4,4a,5,6-tetrahydrobenzo[h]cinnolin-3(2H)-one, melting at 159°–160° C.

EXAMPLE 32

9-Chloro-2-(2-pyridyl)-4,4a,5,6-tetrahydrobenzo[h]cinnolin-3(2H)-one, melting at 155°–157° C.

EXAMPLE 33

8-Chloro-2-(4-methylphenyl)-4,4a,5,6-tetrahydrobenzo[h]cinnolin-3(2H)-one, melting at 120°–122° C.

EXAMPLE 34

8-Chloro-2-(4-methylphenyl)-5,6-dihydrobenzo[h]cinnolin-3(2H)-one, melting at 103°–107° C.

EXAMPLE 35

2-(4-Chlorophenyl)-9-methyl-5,6-dihydrobenzo[h]cinnolin-3(2H)-one, melting at 206°–207° C.

EXAMPLE 36

9-Methyl-2-phenyl-5,6-dihydrobenzo[h]cinnolin-3(2H)-one, melting at 173°–175° C.

EXAMPLE 37

9-Methyl-2-phenyl-4,4a,5,6-tetrahydrobenzo[h]cinnolin-3(2H)-one, melting at 134°–135° C.

EXAMPLE 38

9-Methyl-2-(4-methylphenyl)-5,6-dihydrobenzo[h]cinnolin-3(2H)-one, melting at 190°–191° C.

EXAMPLE 39

2-(3-Methoxyphenyl)-9-methyl-4,4a,5,6-tetrahydrobenzo[h]cinnolin-3(2H)-one, melting at 160°–162° C.

EXAMPLE 40

2-(6-Chloro-2-pyridyl)-9-methyl-4,4a,5,6-tetrahydrobenzo[h]cinnolin-3(2H)-one, melting at 175°–177° C.

EXAMPLE 41

2-(4-Chlorophenyl)-9-methoxy-4,4a,5,6-tetrahydrobenzo[h]cinnolin-3(2H)-one, melting at 130°–132° C.

EXAMPLE 42

9-Methoxy-2-(4-methoxyphenyl)-4,4a,5,6-tetrahydrobenzo[h]cinnolin-3(2H)-one, melting at 107°-109° C.

EXAMPLE 43

8,9-Dichloro-2-(4-methoxyphenyl)-4,4a,5,6-tetrahydrobenzo[h]cinnolin-3(2H)-one.

EXAMPLE 44

9-Fluoro-2-(4-methylphenyl)-4,4a,5,6-tetrahydrobenzo[h]cinnolin-3(2H)-one.

EXAMPLE 45

2-(4-Fluorophenyl)-9-methoxy-4,4a,5,6-tetrahydrobenzo[h]cinnolin-3(2H)-one.

EXAMPLE 46

2-(4-Chlorophenyl)-8,9-dimethoxy-4,4a,5,6-tetrahydrobenzo[h]cinnolin-3(2H)-one.

EXAMPLE 47

8-Methoxy-2-(4-methylphenyl)-4,4a,5,6-tetrahydrobenzo[h]cinnolin-3(2H)-one.

EXAMPLE 48

9-Hydroxy-2-(4-methylphenyl)-4,4a,5,6-tetrahydrobenzo[h]cinnolin-3(2H)-one.

EXAMPLE 49

2-(4-Chlorophenyl)-8-hydroxy-4,4a,5,6-tetrahydrobenzo[h]cinnolin-3(2H)-one.

EXAMPLE 50

8,9-Dihydroxy-2-(4-methylphenyl)-4,4a,5,6-tetrahydrobenzo[h]cinnolin-3(2H)-one.

EXAMPLE 51

9-Acetyl-2-(4-Chlorophenyl)-4,4a,5,6-tetrahydrobenzo[h]cinnolin-3(2H)-one.

EXAMPLE 52

9-Amino-2-(4-hydroxyphenyl)-4,4a,5,6-tetrahydrobenzo[h]cinnolin-3(2H)-one.

Although the present invention has been adequately discussed in the foregoing specification and examples included therein, one readily recognizes that various changes and modifications may be made without departing from the spirit and scope of the present invention.

What is claimed is:

1. A benzo[h]cinnoline compound of the formula

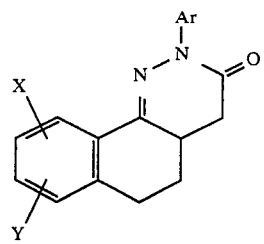

wherein
X is hydrogen, halogen, trifluoromethyl, hydroxy, alkyl having 1 to 4 carbon atoms, alkoxy having 1 to 4 carbon atoms, nitro, cyano or alkanoyl having 2 to 4 carbon atoms, and
Y is hydrogen, halogen, hydroxy or alkoxy having 1 to 4 carbon atoms, with the provisos that
when Y is hydrogen, X is hydrogen, halogen, trifluoromethyl, hydroxy, alkyl having 1 to 4 carbon atoms, alkoxy having 1 to 4 carbon atoms, nitro, cyano or alkanoyl having 2 to 4 carbon atoms,
when Y is halogen, X is hydrogen or hydroxy, and
when Y is alkoxy having 1 to 4 carbon atoms, X is hydrogen or alkoxy having 1 to 4 carbon atoms, and
Ar is phenyl or 2-pyridyl which may be optionally substituted by a substituent selected from the group consisting of halogen, trifluoromethyl, hydroxy, alkyl having 1 to 4 carbon atoms, amino, alkanoylamido having 2 to 4 carbon atoms, nitro and cyano; and the bond position indicated by the dotted line is a single bond or double bond.

2. The compound of claim 1:
2-(4-methoxyphenyl)-9-methyl-4,4a,5,6-tetrahydrobenzo[h]cinnolin-3(2H)-one.

3. The compound of claim 1:
9-chloro-2-(4-methylphenyl)-4,4a,5,6-tetrahydrobenzo[h]cinnolin-3(2H)-one.

4. The compound of claim 1:
2-(4-chlorophenyl)-9-fluoro-5,6-dihydrobenzo[h]cinnolin-3(2H)-one.

5. The compound of claim 1:
2-(4-chlorophenyl)-9-fluoro-4,4a,5,6-tetrahydrobenzo[h]cinnolin-3(2H)-one.

6. The compound of claim 1:
9-fluoro-2-phenyl-5,6-dihydrobenzo[h]cinnolin-3(2H)-one.

7. The compound of claim 1:
2-(4-chlorophenyl)-9-methoxy-4,4a,5,6-tetrahydrobenzo[h]cinnolin-3(2H)-one.

8. The compound of claim 1:
9-methoxy-2-(4-methoxyphenyl)-4,4a,5,6-tetrahydrobenzo[h]cinnolin-3(2H)-one.

9. A pharmaceutical composition for use as an antidote for benzodiazepine-induced oversedation or for use as an antianxiety agent comprising a therapeutically effective amount of a compound of claim 1 and a pharmaceutically acceptable carrier therefor.

* * * * *